United States Patent [19]

Bessler et al.

[11] Patent Number: 5,197,649
[45] Date of Patent: Mar. 30, 1993

[54] GASTROINTESTINAL ENDOSCOPTIC STAPLER

[75] Inventors: Marc Bessler; Michael R. Treat, both of New York, N.Y.

[73] Assignee: The Trustees of Columbia University in the City of New York, New York, N.Y.

[21] Appl. No.: 783,909

[22] Filed: Oct. 29, 1991

[51] Int. Cl.⁵ .............................................. A61B 17/00
[52] U.S. Cl. ..................................... 227/179; 227/180; 227/19; 227/156; 128/4
[58] Field of Search ............................. 227/178-181, 227/19; 128/4

[56] References Cited

U.S. PATENT DOCUMENTS

| | | |
|---|---|---|
| 3,193,165 | 8/1962 | Akhalaya et al. . |
| 3,256,875 | 5/1963 | Tsepelev et al. . |
| 3,388,847 | 6/1968 | Kasulin et al. . |
| 3,552,626 | 1/1971 | Astafiev et al. . |
| 3,858,577 | 1/1975 | Basset et al. . |
| 3,859,986 | 1/1975 | Okada et al. . |
| 4,085,756 | 4/1978 | Weaver . |
| 4,198,960 | 4/1980 | Utsugi . |
| 4,198,982 | 4/1980 | Fortner et al. . |
| 4,202,479 | 5/1980 | Razgulov et al. . |
| 4,207,898 | 6/1980 | Becht . |
| 4,250,873 | 2/1981 | Bonnet . |
| 4,273,109 | 6/1981 | Enderby . |
| 4,273,111 | 6/1981 | Tsukaya .............................. 128/6 |
| 4,287,585 | 9/1981 | Ogawa . |
| 4,289,133 | 9/1981 | Rothfuss . |
| 4,304,236 | 12/1981 | Conta et al. . |
| 4,310,115 | 1/1982 | Inoue . |
| 4,319,576 | 3/1982 | Rothfuss . |
| 4,351,466 | 9/1982 | Noiles . |
| 4,367,729 | 1/1983 | Oglu . |
| 4,379,457 | 4/1983 | Gravener et al. . |
| 4,445,892 | 5/1984 | Hussein et al. . |
| 4,448,188 | 5/1984 | Loeb . |
| 4,473,077 | 9/1984 | Noiles et al. . |
| 4,476,863 | 10/1984 | Kanshin et al. . |
| 4,485,817 | 12/1985 | Swiggett . |
| 4,488,523 | 12/1985 | Shichman ........................... 227/179 |
| 4,499,895 | 2/1985 | Takayama . |
| 4,505,272 | 3/1985 | Utyamyshev et al. . |
| 4,505,414 | 3/1985 | Filipi . |
| 4,559,928 | 12/1985 | Takayama . |
| 4,573,468 | 3/1986 | Conta et al. . |
| 4,574,806 | 3/1986 | McCarthy . |
| 4,576,167 | 3/1986 | Noiles ................................. 227/179 |
| 4,589,412 | 5/1986 | Kensey . |
| 4,592,354 | 6/1986 | Rothfuss . |
| 4,593,679 | 6/1986 | Collins ................................ 128/4 |
| 4,603,693 | 8/1986 | Conta et al. . |
| 4,606,343 | 8/1986 | Conta et al. . |
| 4,610,383 | 9/1986 | Rothfuss et al. . |
| 4,646,745 | 3/1987 | Noiles . |

(List continued on next page.)

Primary Examiner—Stephen C. Pellegrino
Assistant Examiner—Gary Jackson
Attorney, Agent, or Firm—John P. White; Peter J. Phillips

[57] ABSTRACT

An intestinal steerable endoscopic stapler for stapling tubular tissue is provided comprising a circular anvil member having a circular anvil stapling surface and a cutting block surface radially inwardly of the stapling surface. A head assembly has a circular staple driver for driving staples in an array corresponding to the anvil surface and a circular cutting blade corresponding to the cutting block. A flexible tube has a distal end at the head assembly and a handpiece end. A scope in the form of an eyepiece in the handpiece optically connected to a lens in the head assembly is provided for viewing a region of space beyond the head assembly. A steering arrangement is provided for pivoting the head assembly relative the flexible tube to thereby steer the head assembly in a body cavity. A stapler activator is provided located at the handpiece end and for driving staples from the head assembly toward the anvil member and for driving the cutting blade toward the cutting block, whereby two ends of tubular tissue may be joined by an array of annular staples and excess tubular tissue ends may be trimmed off with the cutting blade.

58 Claims, 6 Drawing Sheets

U.S. PATENT DOCUMENTS

| | | |
|---|---|---|
| 4,667,673 | 5/1987 | Li . |
| 4,671,445 | 6/1987 | Barker et al. . |
| 4,672,961 | 6/1987 | Davies . |
| 4,696,667 | 9/1987 | Masch . |
| 4,700,703 | 10/1987 | Resnick et al. . |
| 4,703,887 | 11/1987 | Clanton et al. . |
| 4,708,141 | 11/1987 | Inoue et al. . |
| 4,752,024 | 1/1988 | Green et al. . |
| 4,754,909 | 7/1988 | Barker et al. . |
| 4,756,309 | 7/1988 | Sachse et al. . |
| 4,760,840 | 8/1988 | Fournier Jr. et al. . |
| 4,776,506 | 10/1988 | Green . |
| 4,817,847 | 4/1989 | Redtenbacher et al. . |
| 4,819,632 | 4/1989 | Davies . |
| 4,873,977 | 10/1989 | Avant et al. . |
| 4,893,622 | 1/1990 | Green et al. . |
| 4,903,697 | 2/1990 | Resnick et al. . |
| 4,907,591 | 3/1990 | Vasconcellos et al. . |
| 4,917,114 | 4/1990 | Green et al. . |
| 4,957,499 | 9/1990 | Lipator et al. ..................... 227/180 |
| 4,962,877 | 10/1990 | Hervas . |
| 4,976,710 | 12/1990 | Mackin . |
| 4,994,060 | 2/1991 | Rink et al. . |

FOREIGN PATENT DOCUMENTS

| | | |
|---|---|---|
| 3300768 | 4/1985 | Fed. Rep. of Germany . |
| 7711347 | 10/1987 | Netherlands . |

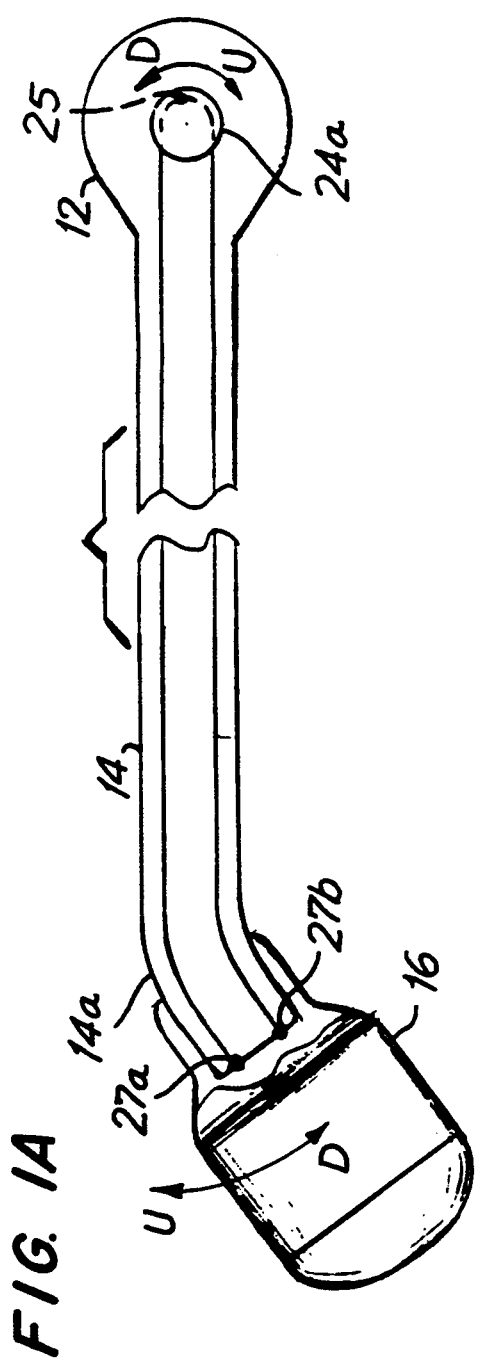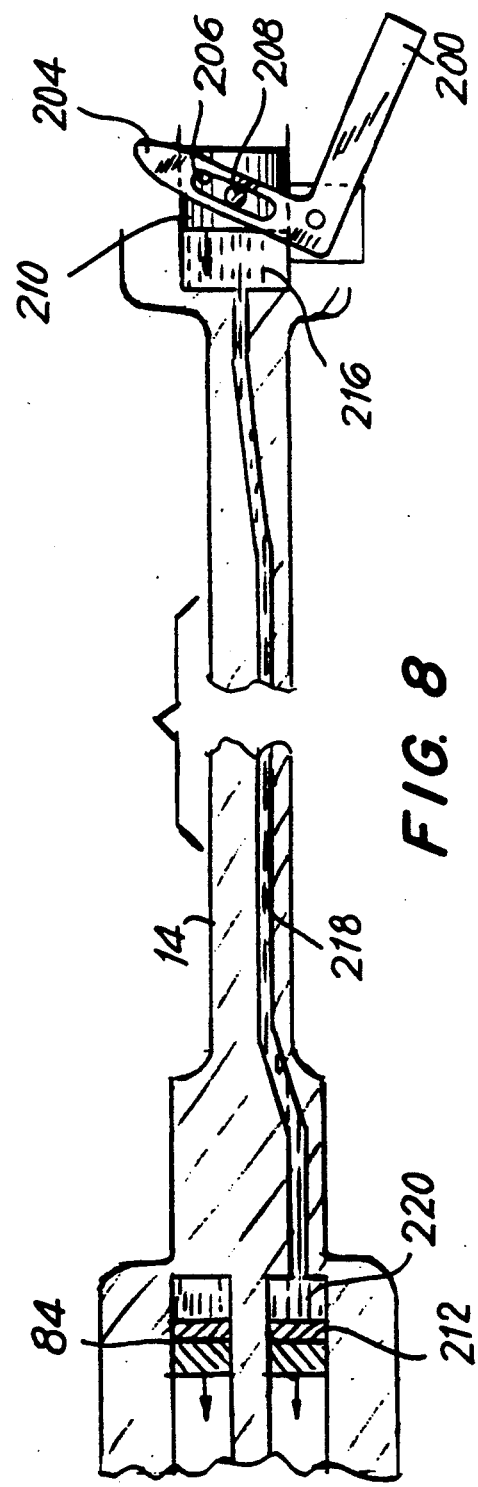
FIG. 1A
FIG. 8

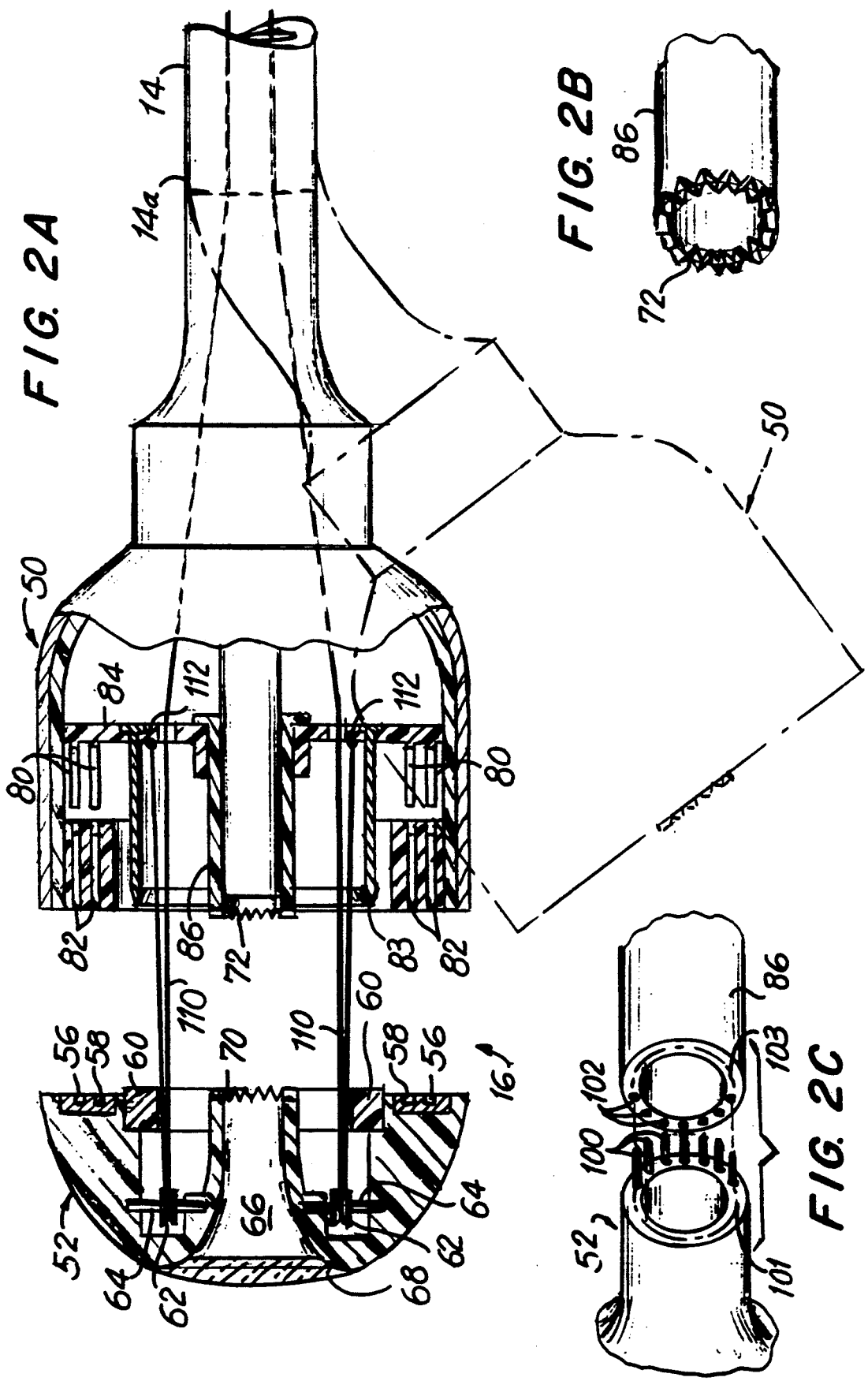

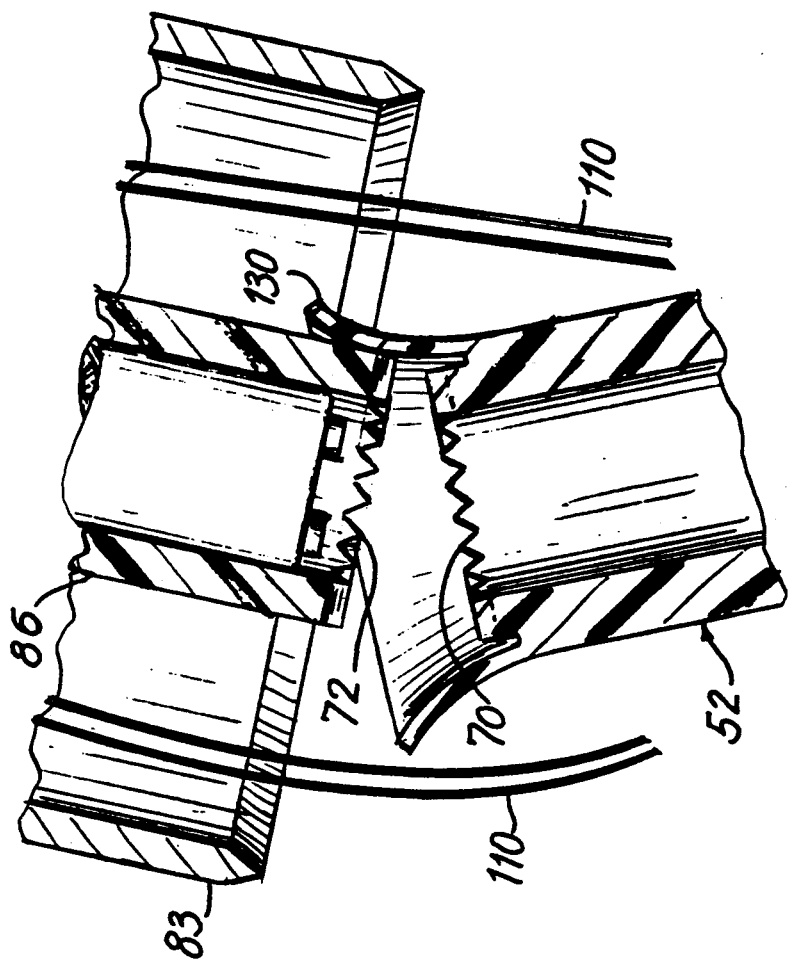
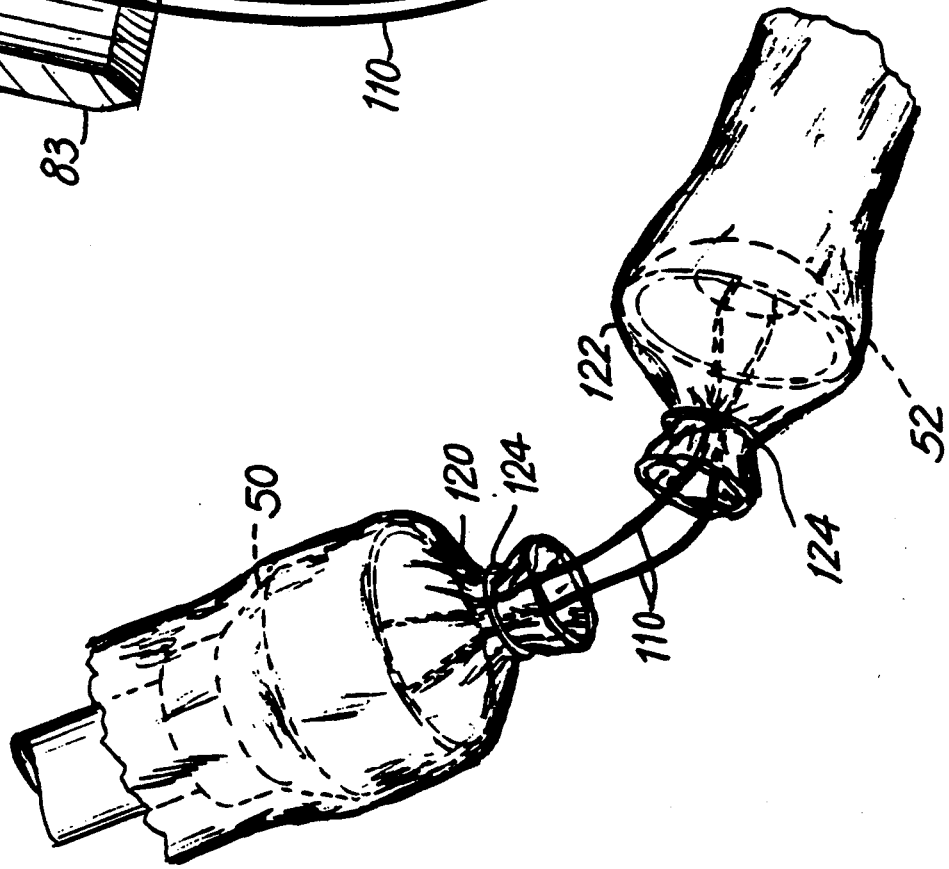

GASTROINTESTINAL ENDOSCOPTIC STAPLER

BACKGROUND OF THE INVENTION

This invention relates to a surgical stapling apparatus, and more particularly to a surgical stapling apparatus for effecting closure of circular anastomosis.

A colon resection operation involves removing a section of the tubular colon which has become diseased and then joining the ends in an end-to-end anastomosis ("EEA"). Approximately 100,000 colon resections are performed each year in the United States, 70% of which are distal to the right colon. Although gastrointestinal anastomosis ("GIA") stapling devices are available for some colon resections, most surgeons do not use such devices to create left sided colonic anastomosis, and only about 15% of colon anastomosis are within reach of the existing EEA devices through the rectum.

Various types of circular anastomosis stapler devices are available for effecting end-to-end circular anastomosis stapling. Examples of such devices are described in U.S. Pat. No. 4,752,024, U.S. Pat. No. 4,485,817 and patents cited therein. Such stapling devices typically comprise a fastener holding assembly and an anvil assembly located at the distal end of a stapling mechanism, with means to control the spacing distance between the anvil assembly and fastener holding assembly. During surgical operations, when a surgeon desires to join by stapling two ends of tubular tissue, such as a colon in a colon resection operation, the device is inserted through the colon so that the cut between the two colon sections is disposed in a space between the anvil and stapling mechanism. Purse string-like sutures are made in both colon ends with the sutures pulled tight. A mechanism then pulls the anvil and the stapling mechanism together whereby one or more staples effect an annular stapling function, and a circular cutting blade disposed radially inwardly of the annular stapling array cuts out the remaining tissue radially inwardly of the annular staple ring. The apparatus is then removed from the colon, leaving a clean cut line and an annular array of staples holding the two previously unjoined colon portions together.

While the above-described devices have been effective for making end-to-end anastomosis, many of these devices suffer from disadvantages. Many of the available devices have a rigid structure which preclude their application for other than straight intestines. Some of these devices additionally suffer from a disadvantage in that anastomosis may be effected only for a limited distance from the entrance cavity, such as the rectum. While some of these devices have employed flexible structure such as a flexible sheath or tube to enable their application to curved intestines, such devices do not provide means for steering the device through a curved section of an intestine, or to branch the device to a selected one of two or more branches in an intestine. Further, these devices also fail to provide means for viewing the surgical site or an interior human cavity on route to the surgical site.

SUMMARY OF THE INVENTION

It is an object of the present invention to provide a surgical stapler apparatus which is flexible to enable its application for curved intestines or the like.

It is an object of the present invention to provide a device which effects creation of a stapled end-to-end, end-to-side or side-to-side anastomosis virtually anywhere in the gastrointestinal tract.

It is another object of the present invention to provide a stapling device having a steering capability to steer the head of the device to a desired location along curved intestines or other surfaces or passageways in a surgical subject.

It is another object of the present invention to provide a surgical stapling device having means for viewing the surgical site as well as for viewing the travel of the device on route to the surgical site.

It is another object of the present invention to provide a surgical stapling device having means for viewing the surgical site from inside the intestine before, during and after stapling.

According to the present invention, an intestinal endoscopic stapler tubular tissue is provided comprising an anvil member having a ringed anvil stapling surface and a ringed cutting block surface inwardly of said stapling surface. A head assembly is provided having a staple driver for driving staples in an array corresponding to the anvil surface and a cutting blade corresponding to the cutting block. A flexible tube is provided having a distal end at the head assembly and a handpiece end. Scope means are provided for viewing a region of space beyond the head assembly. Stapler activating means are also provided located at the handpiece end for driving staples from the head assembly toward the anvil member and for driving the cutting blade toward the cutting block, whereby two ends of tubular tissue may be joined by a ringed array of staples and excess tubular tissue ends may be trimmed off with the cutting blade.

Also in accordance with the present invention, an intestinal steerable surgical stapler is provided comprising an anvil member having a ringed anvil stapling surface and a ringed cutting block surface inwardly of the stapling surface. A head assembly is provided having a staple driver for driving staples in an array corresponding to the anvil surface and a cutting blade corresponding to the cutting block. Also provided is a flexible tube having a distal end at the head assembly and a handpiece end. Steering means are provided for pivoting the head assembly relative to the flexible tube, to thereby steer the head assembly in a body cavity. Stapler activating means are also provided located at the handpiece end for driving staples from the head assembly toward the anvil member and for driving the cutting blade toward the cutting block, whereby two ends of tubular tissue may be joined by a ringed array of staples and excess tubular tissue ends may be trimmed off with the cutting blade.

According to another form of the present invention, an intestinal steerable endoscopic stapler is provided comprising an anvil member having a ringed anvil stapling surface and a ringed cutting block surface inwardly of the stapling surface. A head assembly is provided having a staple driver for driving staples in an array corresponding to the anvil surface and a cutting blade corresponding to the cutting block. A flexible tube has a distal end at the head assembly and a handpiece end. Scope means are provided for viewing a region of space beyond the head assembly. Steering means are provided for pivoting the head assembly relative the flexible tube to thereby steer the head assembly in a body cavity. Stapler activating means are also provided located at the handpiece end and for driving staples from the head assembly toward the anvil member and for driving the cutting blade toward the cutting block, whereby two ends of tubular tissue may be joined by a ringed array of staples and excess tubular tissue ends may be trimmed off with the cutting blade.

Other objects and features of the invention will become apparent from the following detailed description of a preferred embodiment of the invention, taken in conjunction with the accompanying figures.

BRIEF DESCRIPTION OF THE FIGURES

FIG. 1A is a cross-sectional view of the flexible tube, and steering mechanism;

FIG. 2A is a perspective view of the stapling head mechanism and anvil, in partial cross-section, of a first embodiment according to the present invention;

FIG. 2B is a perspective view of the alignment surface of the head mechanism of that shown in FIG. 2A;

FIG. 2C is a perspective view of the different alignment arrangement from that of FIGS. 2A and 2B, for the anvil member and head mechanism;

FIG. 4 is a perspective view of two ends of tubular tissue having purse string sutures, one tubular end of which encloses the anvil portion, and the other tubular section of which encloses the head mechanism, of the embodiment of FIG. 2;

FIG. 5 is a side view in cross-section of the mating surfaces of a head mechanism and anvil of the embodiment of FIG. 2;

FIG. 8 is a cross-sectional view of the hydraulic actuator according to the invention, for driving staples and cutting tissue.

DETAILED DESCRIPTION OF THE PREFERRED EMBODIMENT

Figure 1:
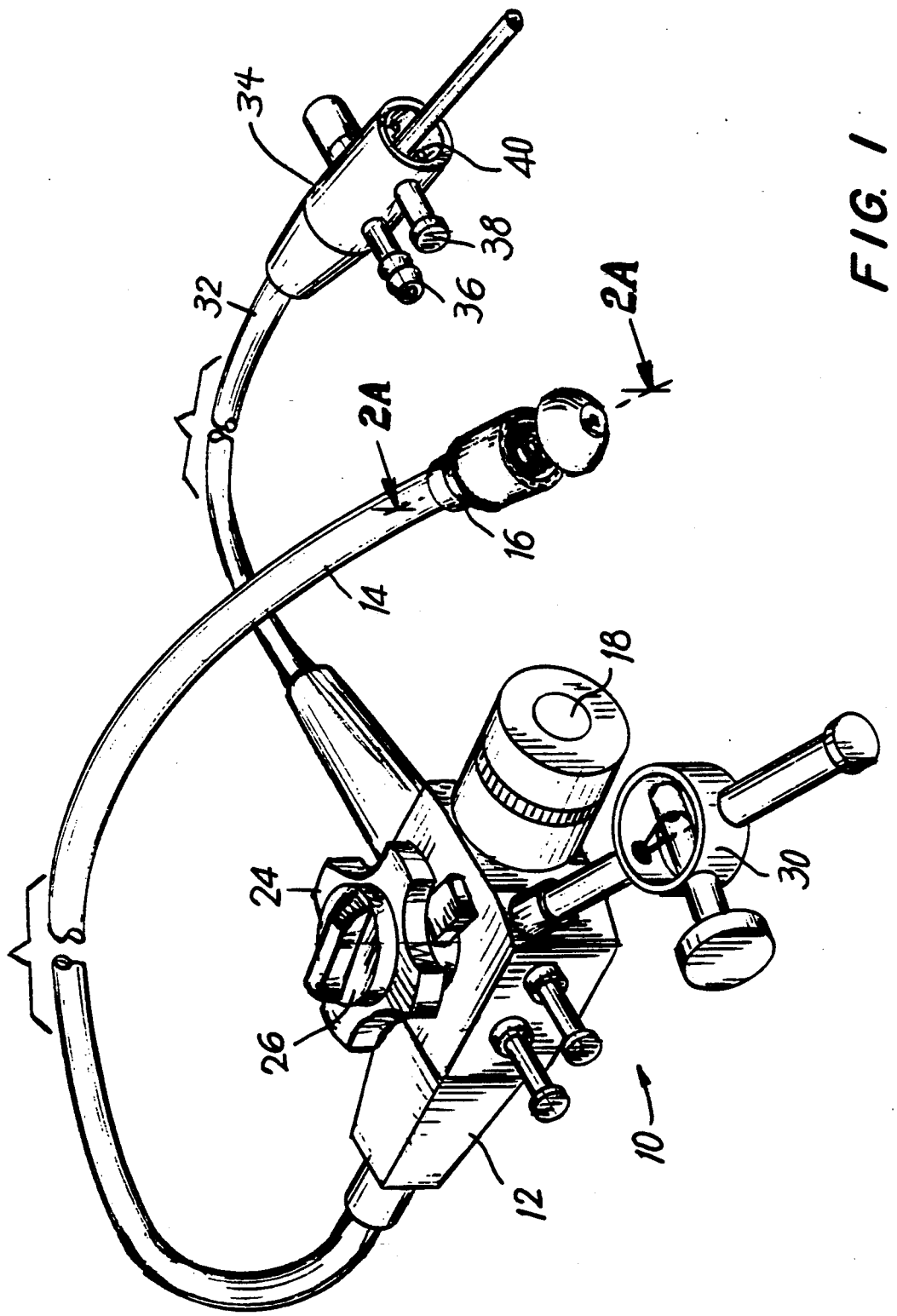
FIG. 1 is a perspective view of the stapling mechanism according to the invention, having a flexible tube, scope and steering features.

According to the present invention, an intestinal staplescope for stapling tubular tissue is provided comprising an anvil member having a ringed anvil stapling surface and a ringed cutting block surface inwardly of said stapling surface. A head assembly is provided having a staple driver for driving staples in an array corresponding to the anvil surface and a cutting blade corresponding to the cutting block. A flexible tube is provided having a distal end at the head assembly and a handpiece end. Scope means are provided for viewing a region of space beyond the head assembly. Stapler activating means are also provided located at the handpiece end for pulling the anvil member and head assembly toward each other, for driving staples from the head assembly toward the anvil member and for driving the cutting blade toward the cutting block, whereby two ends of tubular tissue may be joined by a ringed array of staples and excess tubular tissue ends may be trimmed off with the cutting blade.

The anvil stapling surface and cutting block surface are preferably circular, for driving an annular array of staples. The staplescope preferably has steering means for pivoting said head assembly relative to said flexible tube, to thereby steer the head assembly in a body cavity. Light emitting means are provided, on said distal end, for emitting light into the region of space. The head assembly has watering means for emitting water across said lens means. The staple driver comprises means for driving staples in two concentric circles.

In one embodiment or variation, the stapler activating means comprises a common mount for said staple driver and cutting blade, the common mount being slidably movable axially within said head assembly, pulley means on said anvil, and at least one cable means extending the length of the flexible tube from the handpiece end to the distal end, said cable means distal end passing through said pulley means and being attached to the common mount facing the anvil, to effect driving of staples and cutting of the ends of tubular tissue when the cable means is pulled at the handpiece end. In this first embodiment or variation, the stapler activating means comprises two cables, two pulleys mounted on opposed sides of the anvil, and wherein the two cables are attached to the common mount at opposed sides.

Axial positioning means are provided for positioning said anvil and head assembly in axial alignment when the anvil and head assembly are pulled toward each other. Rotational positioning means are provided for positioning said anvil and head assembly in rotational alignment when said anvil and head assembly are pulled toward each other, so that staples driven from said head assembly in said array are directed toward a corresponding array of anvil stapling positions. Means are provided for holding the stapling surface and anvil surface at least a selected distance apart to avoid crushing tissue during stapling operations. Means are provided for adjusting said selected distance. In one form, a first serrated circular surface is provided on said anvil and a second serrated circular mating surface is provided on said head assembly for positioning the anvil and head assembly in axial and rotational alignment and a selected distance apart during stapling operations when the anvil and head assembly are pulled together. In another form, a ring of pins on said anvil member and a corresponding ring of holes formed in said head assembly for positioning the anvil member and head assembly in axial and rotational alignment and a selected distance apart during stapling operations when the anvil member and head assembly are pulled together.

In another embodiment or variation, provided are a cylindrical sleeve centrally axially located on said anvil, and an axially centrally disposed cylindrical post located on said head assembly, said post being slidingly received in said anvil cylindrical sleeve, for axially aligning said anvil and head assembly. An axial slot on the outer surface of said post, said slot adapted to receive a guide pin extending radially on the cylindrical sleeve for rotationally aligning said anvil member and head assembly, said slot having a selected length which determines the minimum and maximum distance of travel of said anvil stapling surface from said staple driver.

The stapler activating means comprises a cable extending the length of the flexible tube from the handpiece end to the distal end, said cable means distal end being attached to the anvil member whereby pulling the other end of the cable at the handpiece end pulls said head assembly and anvil member toward each other to a selected spacing distance. The stapler activating means comprises a common mount for the staple driver and cutting blade, said common mount being slidably movable axially within said head assembly, and hydraulic means for driving said common mount axially toward said anvil to drive staples and effect cutting of tubular ends of tissue when said head assembly and anvil member are at a selected spacing distance.

Also in accordance with the present invention, an intestinal steerable surgical stapler for stapling tubular tissue is provided comprising an anvil member having a ringed anvil stapling surface and a ringed cutting block surface inwardly of the stapling surface. A head assembly is provided having a staple driver for driving staples in an array corresponding to the anvil surface and a cutting blade corresponding to the cutting block. Also provided is a flexible tube having a distal end at the head assembly and a handpiece end. Steering means are provided for pivoting the head assembly relative to the flexible tube, to thereby steer the head assembly in a body cavity. Stapler activating means are also provided located at the handpiece end for driving staples from the head assembly toward the anvil member and for driving the cutting blade toward the cutting block, whereby two ends of tubular tissue may be joined by a ringed array of staples and excess tubular tissue ends may be trimmed off with the cutting blade.

According to another form of the present invention, an intestinal steerable endoscopic stapler for stapling tubular tissue is provided comprising an anvil member having a ringed anvil stapling surface and a ringed cutting block surface radially inwardly of the stapling surface. A head assembly is provided having a staple driver for driving staples in an array corresponding to the anvil surface and a cutting blade corresponding to the cutting block. A flexible tube has a distal end at the head assembly and a handpiece end. Scope means are provided for viewing a region of space beyond the head assembly. Steering means are provided for pivoting the head assembly relative the flexible tube to thereby steer the head assembly in a body cavity. Stapler activating means are also provided located at the handpiece end for the pulling the anvil member and head assembly toward each other and for driving staples from the head assembly toward the anvil member and for driving the cutting blade toward the cutting block, whereby two ends of tubular tissue may be joined by a ringed array of staples and excess tubular tissue ends may be trimmed off with the cutting blade.

FIG. 1 shows in perspective view, a gastrointestinal endoscopic stapler 10 according to the present invention. A endoscopic stapler comprises a handpiece 12, a flexible tube 14 and a stapling head 16 attached to the distal end of the flexible tube. Details of the stapling head 16, including the stapling head assembly and anvil member, will be described below primarily in conjunction with other figures.

The handpiece 12 comprises scope means in the form of an eyepiece 18 which is optically coupled by means of an optical fiber or the like to a lens means 20 in the stapling head 16. The handpiece 12 also comprises steering control means in the form of two control knobs 24, 26 one of which controls the swiveling of stapling head with respect to the flexible tube 14 in a first plane, while the other knob provides for swiveling of the stapling head 16 in a second plane perpendicular to the first plane. Together the two control knobs 24, 26 provide means for positioning the stapling head at virtually any bending angle relative to the generally central axis of the flexible tube near the vicinity of the stapling head.

FIG. 1A shows, in cross-section, a flexible tube 14 and steering mechanism. The flexible tube has a resilient head portion 14a, to which the stapling head 16 is attached. The resilient head 14a is more flexible then the flexible tube 14. The handpiece 12 has two pulleys, one pulley 24a being shown, which is connected to control knob 24 (not shown in FIG. 1A). Pinned to the pulley at pin point 25 is a cable 27 having one end 27a connected to the end of the resilient head portion 14a, and its other end 27b connected to the resilient head portion 14a at a diametrically opposed location to the connection of 27a. The cable 27 is channeled along its length in a suitable lumen or conduit (not shown) in flexible tube 14. By turning control knob 24 in the U(Up) or D(Down) direction, the pulley 24a will effect swivelling or bending of the resilient head portion 14a, relative to the flexible tube 14, in the U(Up) or D(Down) direction, respectively. (See also phantom lines of head assembly 50 in FIG. 2A). A similar arrangement is provided for control knob 26 for side-to-side swivelling control. Together, the two control knobs 24 and 26 provide means for positioning the stapling head 16 at virtually any desired bending angle. Further details of other bend angle positioning devices which may be used herein may be found in U.S. Pat. Nos. 4,273,111 and 4,286,585, which are incorporated by reference herein.

The handpiece also has extending from it a cable reel device 30 adapted to provide tension to and reel in, in a fishing reel like manner, a cable which extends throughout the length of the flexible tube and terminating in the distal end at the stapling head.

Also attached to the hand is a second flexible tube 32 which terminates at its other end in second handpiece or instrument head 34 which provides an irrigation port 36, a suction port 38, and electrical connectors 40 for connecting to a video monitor whereby the image viewable through the lens can be displayed on a video monitor, and to a power supply for energizing a light source in the stapling head. Many of the features of the scope and steering aspects of the device shown in FIG. 1, except for the stapling head 16, may be found in an instrument available from Olympus Optical Co., Ltd., as Model GIF Type XQ Scope.

Referring now to FIG. 2A, a first variation of a stapling head 16 useable in the device of FIG. 1 will now be described. The stapling head 16 comprises two major portions, a head assembly 50 connected to the distal end of a flexible tube, and an anvil member 52. The anvil member 52 has a circular anvil stapling surface 54 in the form of two concentric rings 56,58 to provide two concentric rings of equally spaced staple anvil patterns each pattern of which is similar to the anvil for a conventional paper stapler whereby a U-shaped staple driven toward the anvil will curve the two points first toward each other and then flat against the base portion of the staple to fasten material which has been pierced by the staple points. The anvil member 52 also comprises a circular or annular cutting block 60 disposed radially inwardly of the stapling anvil surface 54. The anvil member 52 also comprises two pulleys 62 arranged diametrically opposed from each other which are mounted on respective pins 64 and a central opening 66 which may have a clear window 68 of plastic or the like at the front end of the anvil member 52. The anvil member 52 also has a serrated annular 70 surface adapted to mate with a similar serrated annular surface on the head assembly 50, similar to the perimeter serrated surfaces on checkers to mate them when stacking.

The head assembly 50 has a circular staple driver assembly for driving staples in a circular array corresponding to the anvil surface, and more particularly has two rings of drivers 80 and two rings of corresponding staple holder holes 82 for driving a pattern of two annular rings of staples each ring having a equal number of equally spaced staple drivers, but with one ring rotationally offset with respect to the other ring to provide an overlapping of staples throughout the circumferential extent of the stapling pattern. This pattern of two concentric offset rings corresponds to the anvil pattern shown in part in FIG. 3. This results in a pattern of staples which minimizes or eliminates leakage of the colon after stapling. Disposed radially inwardly of the staple drivers 80 is a circular annular cutting blade 83 corresponding in size to the cutting block 60 of the anvil member 52. The staple drivers 80 and cutting blade 83 are mounted on a common mount 84 which is movable axially with respect to the exterior housing of the head assembly 50 and staple holder holes 82. As those skilled in the art will appreciate, the stapling surface 54, cutting block 60, and corresponding portions of the head assembly may be any ringed configuration other than truly circular, such as oval, elliptical, etc.

Figure 3:
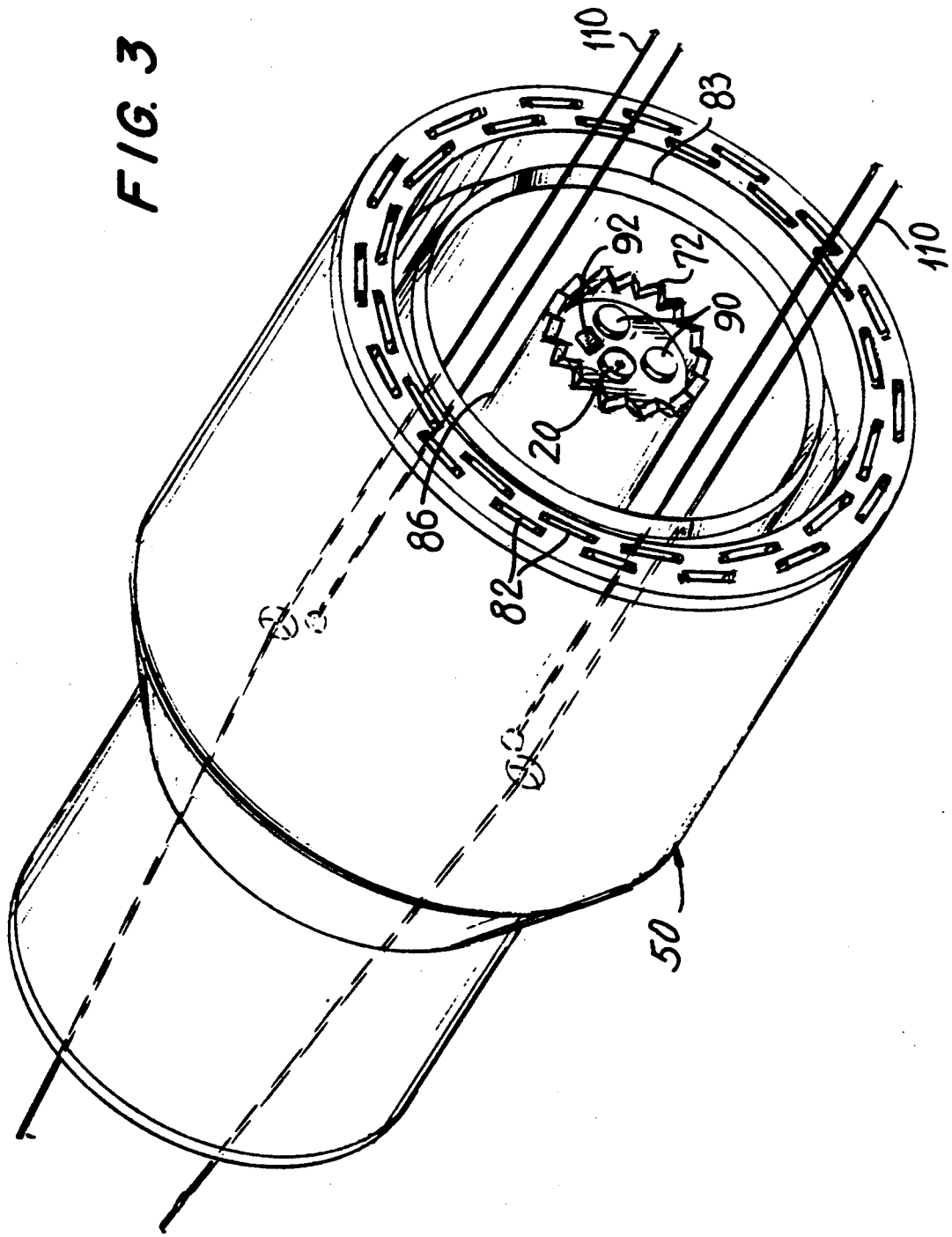
FIG. 3 is a perspective view of the stapling head mechanism of the embodiment of FIG. 2.

Disposed in the interior central portion of the head assembly 50 is a cylindrical body 85 which, as shown in more detail in FIG. 3, has two light emitting means 90, an optical lens 20, and a washing head 92. The light emitting means 90 are connected a source of light at the handpiece 12 or 34, and the lens 20 is optically connected to the eyepiece 18 of FIG. 1. The washing head 92 is connected to the irrigation port connector 36 on the second handpiece or instrument head 34 of FIG. 1, and provides a means for spraying water across the lens 20 to cleanse it.

The front surface of the cylindrical body 86 has a mating serrated surface 72 (shown in greater detail in FIG. 2B), which as described above mates with the serrated surface 70 of the anvil member 52. The serrated mating surfaces 70,72 provide a means for axially aligning the anvil member 52 with the head assembly 50. The number of serrations in each of the two serrated surfaces equals the number of anvil patterns in one of the annular rings of the staple driver assembly and anvil surface, so that when the anvil member 52 is positioned in mating arrangement with the head assembly 50, the staple drivers 80 and staple holder holes will be rotationally aligned with the anvil stapling pattern rings 56,58. The serrated surfaces 70,72 are positioned axially to provide a selected minimum distance between the anvil member 52 and head assembly 50 so as to avoid crushing of tissue located between the head assembly 50 and anvil member 52 during a stapling operation, which will be described below. The positioning of one or both of the serrated surfaces within their respective members may be adjustable, if desired, to provide means for providing an adjustable selected minimum distance between the anvil member 50 and stapling head 52.

Shown in FIG. 2C is an alternative arrangement for providing alignment of the anvil member 52 and head assembly 50. Here a circular array of pins 100 are arranged in a pattern corresponding to a circular array of funneling holes 102 in a cylindrical body 86. The pins 100 can thus pierce tissue which may be in the way of holes 102. The funneling holes 102 guide the pins 100 to mate in the holes even if initially out of rotational and/or axial alignment. The number of pins 100 and holes 102 preferably equals the number of anvil patterns and staple holes/drivers in one ring, and are rotationally positioned so that the staple holes/drivers align with the anvil patterns when the pins 100 align with the holes 102 in any rotational position. The depth of the holes 102 is longer than the pins 100 so that the surface 101 which the pins extend will be located a selected minimum distance away from surface 103 on which the holes are formed when the pins 100 are received in the holes to their full depth.

Also shown in FIG. 2A are two cables 110 each of which wraps around a different pulley 62 in the anvil member 52 and is attached at its end 112 to the common mount 84 holding the cutting blade 83 and the staple drivers 80. The two cables 110 are located on diametrically opposed sides of both the anvil member 50,52 and head assembly 50, and extend through the entire length of the flexible tube 14, terminating at the reel mechanism 30 as shown in FIG. 1. By turning the reel mechanism 30 to provide tension to the cable, the anvil member 52 will be pulled against the head assembly 50, whereby the serrated surfaces 70,72 will mate to provide axial and rotational alignment, and thereafter provide for axially moving the common mount 84 containing the cutting blade 82 and staple drivers 80 toward the anvil member 50 to effect a stapling and cutting function as will be described below. The cables 110 enter the flexible tube 14 not at the end of the sleeve 86, but at a distance from the distal end as shown in FIG. 2A.

Referring now to FIG. 4, two ends 120,122 of tubular colon tissue are shown, with one end 122 wrapped around the anvil member 50 and the other end wrapped around the head assembly 50. In a surgical colon resection operation for example, the distal end of the flexible tube is inserted through the rectum and by viewing through the eyepiece 18, and using other external devices known to those skilled in the art, such as ultrasound and other imaging systems, the distal end can be positioned at a desired location, such as a colon resection location. A portion of the colon which has been diseased will have been cut away using different, invasive surgical tools, leaving two unjoined sections of tubular colon 120,122.

By using the light 90 and scope (lens 20, eyepiece 18) of the present invention the head assembly 50 is positioned at the colon resection site, and using external surgical apparatus, the two ends of the colon 120,122 are tied with suture material 124 in purse-string fashion around the anvil member 52 and head assembly 50, respectively. The cables 110 which extend between the head assembly 50 and anvil member 52 are shown exposed between the two tied colon ends. Instead of string-like sutures for tying the colon ends, a flat stapling device may be used.

The reeling mechanism 30 is then operated to apply tension to the two cables 110 pulling the anvil member 52 towards the head assembly 50. It may be desired to not have the colon ends tied too tightly, so that the opening at the end of the colon even after being tied will allow the serrated mating surfaces 70,72 of the head assembly 50 and anvil member 52 to mate. The anvil member 52 may also include a outer funnelling ring 130 as shown in FIG. 5. If the alignment arrangement of FIG. 2B is used, the pins 100 can pierce any tissue getting in the way. After the anvil member 52 is pulled in contact with head assembly 50, further tensioning of the cables with the reel mechanism 30 will effect axial movement of the common mount 84 carrying the cutting blade 83 and staple drivers 80 towards the anvil member 52 to effect a stapling function and cutting away of the tubular ends of the tissue. The device may then be removed from the colon.

Figure 6:
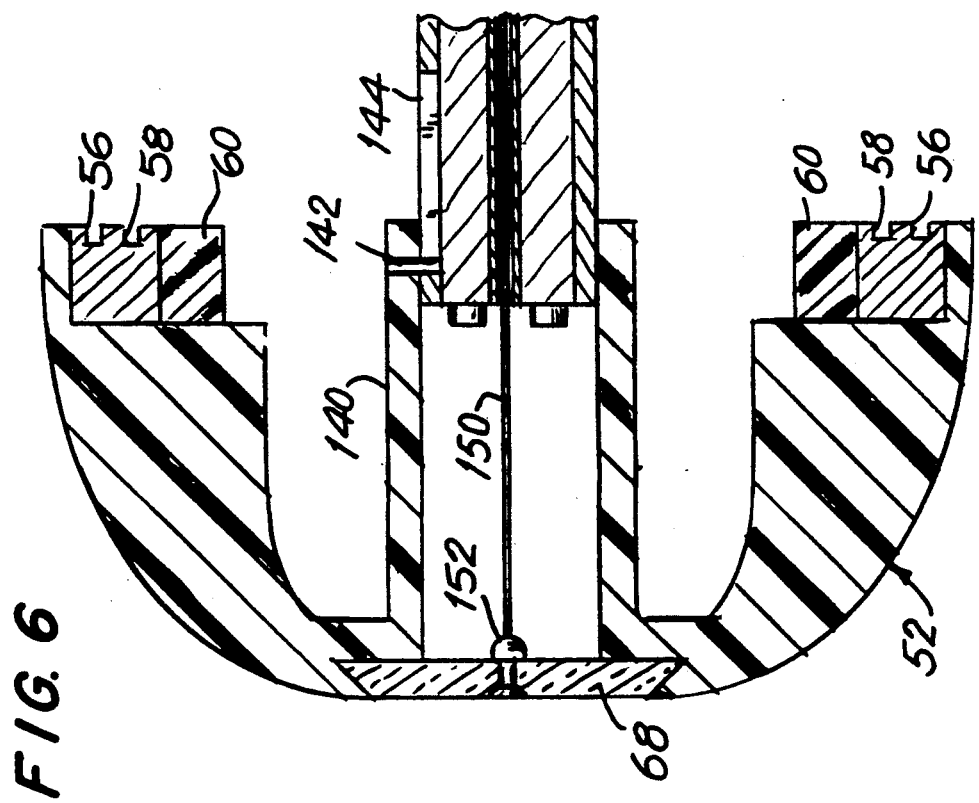
FIG. 6 is a cross-section elevational view of a head mechanism and anvil according to a second embodiment of the present invention.
Figure 7:
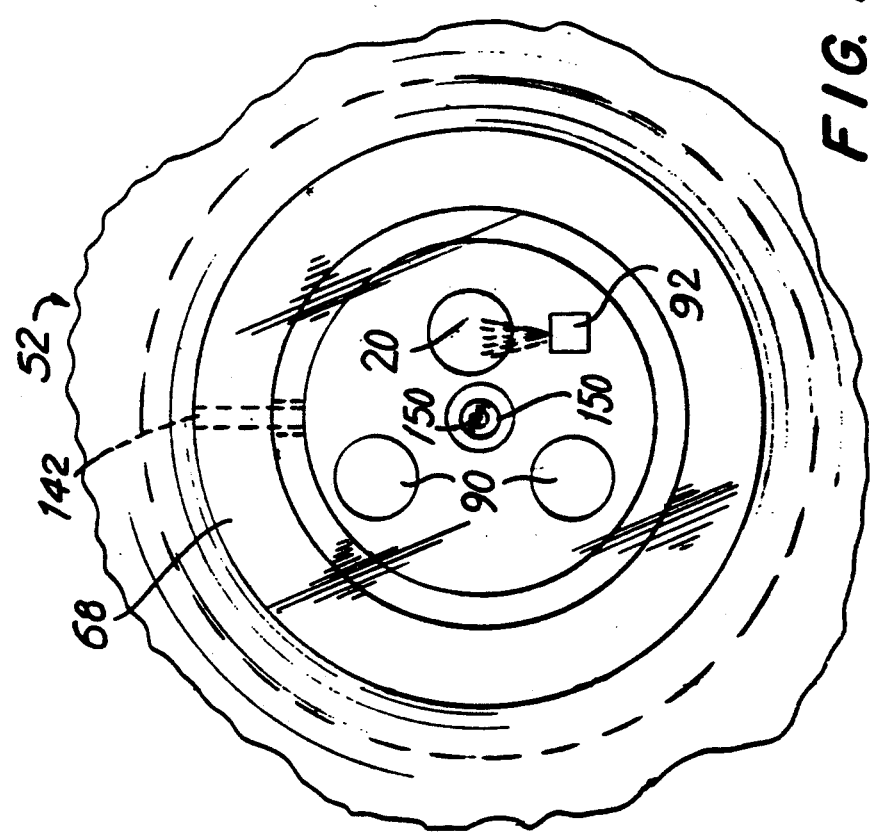
FIG. 7 is an end view of a head mechanism according to the embodiment shown in FIG. 6.

Another variation of the head assembly 50 and anvil member 52 is shown in FIGS. 6 and 7. As shown in FIG. 6, the anvil member 52 includes a cylindrical sleeve 140 having one or more guide pins 142 projecting radially inwardly, which guide pins are received in one or more corresponding slots 144 in the cylinder body 86 of the head assembly 50. This guide pin slot arrangement provides a means for axially and rotationally aligning the anvil member 52 and head assembly 50, as well as providing means for determining the minimum and maximum spacing distances between the anvil member 52 and head assembly 50.

Referring to FIG. 7, which is a front head view of the head assembly 50, a cable 150 is shown exiting a central lumen in the distal end of the flexible tube which cable 150, as shown in FIG. 6 is attached to a pin 152 centrally axially disposed on the front of the anvil member 52. While this cable 150 will be within the field of view of the region of space of the lens 20, only a slight obstruction will result. This single cable 150 performs the same function as the two cables in the first variation, namely to effect pulling of the anvil member 52 toward the head assembly 50 to a position whereby the head assembly 50 and anvil member 52 are at a selected distance close to each other but to not crush the tissue. However, in this embodiment a hydraulic means may be used for transferring force to the common mount 84, from the handpiece 12, to effect stapling by the staple driver and cutting of the tissue to remove the ends of the colon.

FIG. 8 shows an example of a hydraulic means. An actuating lever 200 located at the handpiece 12 has an L-shape and is pivotally mounted at its corner on pin 202. One of its legs 204 has an elongated slot 206 which slidingly receives pin 208 connected to a hydraulic piston 210. Piston 210 when driven to the left in FIG. 8 effects driving of piston 212 by means of hydraulic fluid 214 in cylinder conduit 218 and piston 220, which piston 212 is connected to a common mount 84 to effect driving of staples and cutting of the tissue.

Other hydraulic and/or pneumatic means or the like will readily occur to those skill in the art for effecting transfer of force from the handpiece to the common mount for effecting stapling and cutting of the tissue. In particular, an arrangement may be provided for transforming relatively strong forces to the cutting head to effect stapling and cutting, but wherein the transmitted force along the flexible tube is relatively small to avoid any tendency of the flexible tube to straighten out during the stapling and cutting operation. One such design which may be used is disclosed in U.S. Pat. No. 4,485,817 which is incorporated herein by reference.

The stapling device according to the invention may be constructed for use with existing or general purpose flexible steerable scopes, or a scope may be designed particularly for use with maximizing the efficiency of the stapling mechanism. A removable stapling head and firing mechanism may be attractive to surgeons already having an existing steerable scope and already feel comfortable with its use in surgery while also lowering the cost of a stapling device.

Instead or in addition to a fiberoptic and lens at the end of the head assembly for viewing a region of space, the scope means may comprise a CCD chip at the end of the scope to provide a means for generating a two-dimensional video picture signal, using a video monitor and appropriate electronics connected to the CCD chip.

By providing a gastrointestinal stapling device having a long flexible tube (on the order of about 90 cm), virtually all colon resections could be performed through the rectum and laparoscopically, with minimal invasive surgery. In addition to colon resection, the gastrointestinal stapler could allow laparoscopic esophageal, stomach, proximal and distal small bowel and possibly biliary anastomosis to be performed. Side-to-side or end-to-side, as well as EEA could be performed with the device according to the invention.

Although an embodiment of the invention with variants has been shown and described, it will readily occurred to those skilled in the art that numerous variations and modifications may be effected without departing from the true spirit and scope of the novel concept of the invention, which is limited only by way of the appended claims.

We claim:

1. An intestinal endoscopic stapler for tubular surgical tissue, comprising:
   an anvil member having a ringed anvil stapling surface and a ringed cutting block surface inwardly of said stapling surface;
   a head assembly having a staple driver for driving staples in an array corresponding to said anvil surface and a cutting blade corresponding to said cutting block;
   means for operatively connecting said anvil member to said head assembly;
   a flexible tube having a distal end connected to said head assembly, and a handpiece end;
   scope means, in one of said anvil member and head assembly, for viewing, from said handpiece end, a region of space beyond said head assembly;
   means for pulling said anvil member and said head assembly toward each other; and
   stapler activating means located at the handpiece end, and operatively connected to said anvil member and said head assembly, for driving staples from said had assembly toward said anvil member and for driving said cutting blade toward said cutting block, whereby two ends of tubular tissue may be joined by a ringed array of staples and excess tubular tissue ends may be trimmed off with the cutting blade.

2. The endoscopic stapler according to claim 1, wherein the anvil stapling surface and cutting block surface are circular.

3. The endoscopic stapler according to claim 1, further comprising steering means, in said handpiece end and operatively connected to said head assembly, for pivoting said head assembly relative to said flexible tube, to thereby steer the head assembly in a body cavity.

4. The endoscopic stapler according to claim 1, further comprising light emitting means, located on said distal end and operatively connected to said anvil member and head assembly, for emitting light into the region of space.

5. The endoscopic stapler according to claim 1, wherein said scope means includes lens means, and further comprising watering means for emitting water across said lens means.

6. The endoscopic stapler according to claim 1, wherein said staple driver comprises means for driving staples in two concentric circles.

7. The endoscopic stapler according to claim 1, wherein the stapler activating means comprises:
   a common mount for said staple driver and cutting blade, said common mount being slidably movable axially within said head assembly;
   pulley means on said anvil member; and
   at least one cable means extending the length of the flexible tube from the handpiece end to the distal end, said cable means distal end passing through said pulley means and being attached to the common mount facing the anvil, to effect driving of staples and cutting of the ends of tubular tissue when the cable means is pulled at the handpiece end.

8. The endoscopic stapler according to claim 7, wherein the stapler activating means comprises two cables, two pulleys mounted on opposed sides of the anvil member, and wherein the two cables are attached to the common mount at opposed sides.

9. The endoscopic stapler according to claim 1, further comprising axial positioning means for positioning said anvil member and head assembly in axial alignment when the anvil member and head assembly are pulled toward each other.

10. The endoscopic stapler according to claim 2, further comprising rotational positioning means for positioning said anvil member and head assembly in rotational alignment when said anvil member and head assembly are pulled toward each other, so that staples driven from said head assembly in said circular array are directed toward a corresponding array of anvil stapling positions.

11. The endoscopic stapler according to claim 1, comprising means for holding the stapling surface and anvil surface at least a selected distance apart to avoid crushing tissue during stapling operations.

12. The endoscopic stapler according to claim 11, comprising means for adjusting said selected distance.

13. The endoscopic stapler according to claim 1, further comprising a first serrated circular surface on said anvil member and a second serrated circular mating surface on said head assembly for positioning the anvil member and head assembly in axial and rotational alignment and a selected distance apart during stapling operations when the anvil member and head assembly are pulled together.

14. The endoscopic stapler according to claim 1, further comprising a ring of pins on said anvil member and a corresponding ring of holes formed in said head assembly for positioning the anvil member and head assembly in axial and rotational alignment and a selected distance apart during stapling operations when the anvil member and head assembly are pulled together.

15. The endoscopic stapler according to claim 1, further comprising a cylindrical sleeve centrally axially located on said anvil member, and an axially centrally disposed cylindrical post located on said head assembly, said post being slidingly received in said anvil cylindrical sleeve, for axially aligning said anvil member and head assembly.

16. The endoscopic stapler according to claim 15, including an axial slot on the outer surface of said post, said slot adapted to receive a guide pin extending radially on the cylindrical sleeve for rotationally aligning said anvil member and head assembly, said slot having a selected length which determines the minimum and maximum distance of travel of said anvil stapling surface from said head assembly.

17. The endoscopic stapler according to claim 1, wherein the stapler activating means comprises a cable extending the length of the flexible tube from the handpiece end to the distal end, said cable means distal end being attached to the anvil whereby pulling the other end of the cable at the handpiece end pulls said head assembly and anvil member toward each other to a selected spacing distance.

18. The endoscopic stapler according to claim 1, wherein the stapler activating means comprises:
   a common mount for the staple driver and cutting blade, said common mount being slidably movable axially within said head assembly; and
   hydraulic means for driving said common mount axially toward said anvil member to drive staples and effect cutting of tubular ends of tissue when said head assembly and anvil member are at a selected spacing distance.

19. An intestinal steerable surgical stapler for stapling tubular tissue comprising:
   an anvil member having a ringed anvil stapling surface, and a ringed cutting block surface inwardly of said stapling surface;
   a head assembly having a staple driver for driving staples in an array corresponding to said anvil surface, and a cutting blade corresponding to said cutting block;
   means for operatively connecting said anvil member to said head assembly;
   a flexible tube having a distal end connected to said head assembly, and a handpiece end;
   steering means in said handpiece end and operatively connected to said head assembly, for pivoting said head assembly relative to said flexible tube, to thereby steer the head assembly in a body cavity;
   means for pulling said anvil member and said head assembly toward each other; and
   stapler activating means located at the handpiece end, and operatively connected to said anvil member and said head assembly, for driving staples from said head assembly toward said anvil member and for driving said cutting blade toward said cutting block, whereby two ends of tubular tissue may be joined by a ringed array of staples and excess tubular tissue ends may be trimmed off with the cutting blade.

20. The surgical stapler according to claim 19, wherein the anvil stapling surface and cutting block surface are circular.

21. The surgical stapler according to claim 19, further comprising:
   scope means, in one of said anvil member and head assembly, for viewing, from said handpiece end, a region of space beyond said head assembly.

22. The surgical stapler according to claim 19, further comprising light emitting means, located on said distal end, and operatively connected to one of said anvil member and head assembly, for emitting light into a region of space.

23. The surgical stapler according to claim 19, wherein said scope means includes lens means, and further comprising watering means for emitting water across said lens means.

24. The surgical stapler according to claim 19, wherein said staple driver comprises means for driving staples in two concentric circles.

25. The surgical stapler according to claim 19, wherein the stapler activating means comprises:
   a common mount for said staple driver and cutting blade, said common mount being slidably movable axially within said head assembly;
   pulley means on said anvil member; and
   at least one cable means extending the length of the flexible tube from the handpiece end to the distal end, said bale means distal end passing through said pulley means and being attached to the common mount facing the anvil, to effect driving of staples and cutting of the ends of tubular tissue when the cable means is pulled at the handpiece end.

26. The surgical stapler according to claim 25, wherein the stapler activating means comprises two cables, two pulleys mounted on opposed sides of the anvil member, and wherein the two cables are attached to the common mount at opposed sides.

27. The surgical stapler according to claim 19, further comprising axial positioning means for positioning said anvil member and head assembly in axial alignment when the anvil member and head assembly are pulled toward each other.

28. The surgical stapler according to claim 20, further comprising rotational positioning means for positioning said anvil member and head assembly in rotational alignment when said anvil member and head assembly are pulled toward each other, so that staples driven from said head assembly in said circular array are directed toward a corresponding array of anvil stapling positions.

29. The surgical stapler according to claim 19, comprising means for holding the stapling surface and anvil surface at least a selected distance apart to avoid crushing tissue during stapling operations.

30. The surgical stapler according to claim 29, comprising means for adjusting said selected distance.

31. The surgical stapler according to claim 19, further comprising a first serrated circular surface on said anvil member and a second serrated circular mating surface on said head assembly for positioning the anvil member and head assembly in axial and rotational alignment and a selected distance apart during stapling operations when the anvil member and head assembly are pulled together.

32. The surgical stapler according to claim 19, further comprising a ring of pins on said anvil member and a corresponding ring of holes formed in said head assembly for positioning the anvil member and head assembly in axial and rotational alignment and a selected distance apart during stapling operations when the anvil member and head assembly are pulled together.

33. The surgical stapler according to claim 19, further comprising a cylindrical sleeve centrally axially located on said anvil member, and an axially centrally disposed cylindrical post, located on said head assembly said post being slidingly received in said anvil cylindrical sleeve, for axially aligning said anvil member and head assembly.

34. The surgical stapler according to claim 33, including an axial slot on the outer surface of said post, said slot adapted to receive a guide pin extending radially on the cylindrical sleeve for rotationally aligning said anvil member and head assembly, said slot having a selected length which determines the minimum and maximum distance of travel of said anvil stapling surface from said head assembly.

35. The surgical stapler according to claim 19, wherein the stapler activating means comprises a cable means extending the length of the flexible tube from the handpiece end to the distal end, said cable means distal end being attached to the anvil member whereby pulling the other end of the cable at the handpiece end pulls said head assembly and anvil member toward each other to a selected spacing distance.

36. The surgical stapler according to claim 19, wherein the stapler activating means comprises:
   a common mount for the staple driver and cutting blade, said common mount being slidably movable axially within said head assembly; and
   hydraulic means for driving said common mount axially toward said anvil member to drive staples and effect cutting of tubular ends of tissue when said head assembly and anvil member are at a selected spacing distance.

37. An intestinal steerable endoscopic stapler for stapling tubular tissue comprising:
   an anvil member having a ringed anvil stapling surface, and a ringed cutting block surface inwardly of said stapling surface;
   a head assembly having a staple driver for driving staples in an array corresponding to said anvil surface, and a cutting blade corresponding to said cutting block;
   means for operatively connecting said anvil member to said head assembly;
   a flexible tube having a distal end connected to said head assembly and a handpiece end;
   scope means, in one of said anvil member and head assembly, for viewing, from said handpiece end, a region of space beyond said head assembly;
   steering means, in said handpiece end and operatively connected to said head assembly, for pivoting said head assembly relative to said flexible tube to thereby steer the head assembly in a body cavity;
   means for pulling said anvil member and said head assembly toward each other; and
   stapler activating means located at the handpiece end, and operatively connected to said anvil member and said head assembly, for driving staples from said head assembly toward said anvil member and for driving said cutting blade toward said cutting block, whereby two ends of tubular tissue may be joined by a ringed array of staples and excess tubular tissue ends may be trimmed off with the cutting blade.

38. The endoscopic stapler according to claim 37, wherein the anvil stapling surface and cutting blade surface are circular.

39. The endoscopic stapler according to claim 37, further comprising light emitting means, located on said distal end, and operatively connected to said anvil member and head assembly, for emitting light into the region of space.

40. The endoscopic stapler according to claim 37, wherein said scope means includes lens means, and further comprising watering means for emitting water across said lens means.

41. The endoscopic stapler according to claim 37, wherein said staple driver comprises means for driving staples in two concentric circles.

42. The endoscopic stapler according to claim 37, wherein the stapler activating means comprises:

a common mount for said staple driver and cutting blade, said common mount being slidably movable axially within said head assembly;

pulley means on said anvil member; and at least one cable means extending the length of the flexible tube from the handpiece end to the distal end, said cable means distal end passing through said pulley means and being attached to the common mount facing the anvil, to effect driving of staples and cutting of the ends of tubular tissue when the cable means is pulled at the handpiece end.

43. The endoscopic stapler according to claim 42, wherein the stapler activating means comprises two cables, the pulleys mounted on opposed sides of the anvil member, and wherein the two cables are attached to the common mount at opposed sides.

44. The endoscopic stapler according to claim 37, further comprising axial positioning means for positioning said anvil member and head assembly in axial alignment when the anvil member and head assembly are pulled toward each other.

45. The endoscopic stapler according to claim 38, further comprising rotational positioning means for positioning said anvil member and head assembly in rotational alignment when said anvil member and head assembly are pulled toward each other, so that staples driven from said head assembly in said circular array are directed toward a corresponding array of anvil positions.

46. The endoscopic stapler according to claim 37, comprising means for holding the stapling surface and anvil surface at least a selected distance apart to avoid crushing tissue during stapling operations.

47. The endoscopic stapler according to claim 46, comprising means for adjusting said selected distance.

48. The endoscopic stapler according to claim 37, further comprising a first serrated circular surface on said anvil member and a second serrated circular mating surface on said head assembly for positioning the anvil member and head assembly in axial and rotational alignment and a selected distance apart during stapling operations when the anvil member and head assembly are pulled together.

49. The endoscopic stapler according to claim 37, further comprising a ring of pins on said anvil member and a corresponding ring of holes formed in said head assembly for positioning the anvil member and head assembly in axial and rotational alignment and a selected distance apart during stapling operations when the anvil member and head assembly are pulled together.

50. The endoscopic stapler according to claim 37, further comprising a cylindrical sleeve centrally axially located on said anvil member, and an axially centrally disposed cylindrical post located on said head assembly, said post being slidingly received in said anvil cylindrical sleeve, for axially aligning said anvil member and head assembly.

51. The endoscopic stapler according to claim 50, including an axial slot on the outer surface of said post, said slot adapted to receive a guide pin extending radially on the cylindrical sleeve for rotationally aligning said anvil member and head assembly, said slot having a selected length which determines the minimum and maximum distance of said anvil stapling surface from said head assembly.

52. The endoscopic stapler according to claim 37, wherein the stapler activating means comprises a cable means extending the length of the flexible tube from the handpiece end to the distal end, said cable means distal end being attached to the anvil member whereby pulling the other end of the cable at the handpiece end pulls said head assembly and anvil member toward each other to a selected spacing distance.

53. The endoscopic stapler according to claim 37, wherein the stapler activating means comprises:

a common mount for the staple driver and cutting blade, said common mount being slidably movable axially within said head assembly; and hydraulic means for driving said common mount axially toward said anvil member to drive staples and effect cutting of tubular ends of tissue when said head assembly and anvil member are at a selected spacing distance.

54. An endoscopic surgical stapler comprising:
(a) a stapler assembly which includes:
  (i) an anvil member which defines a tissue engaging surface, said tissue engaging surface including a plurality of anvil pockets; and
  (ii) a head assembly adapted to receive surgical staples within a plurality of staple slots, said head assembly defining a tissue contacting surface which is adapted to align with said tissue engaging surface;
(b) moving means associated with said stapler assembly for moving said anvil member and said head assembly relative to one another between a first, spaced position in which said tissue engaging surface is spaced from said tissue contacting surface for receiving tissue therebetween, and a second approximated position in which said tissue engaging surface and said tissue contacting surface are in close cooperative alignment;
(c) imaging means associated with one of said anvil member and said head assembly for obtaining an image of an interior body region;
(d) an elongated member having a proximal and distal end, said stapler assembly being positioned at and cooperating with said distal end of said elongated member; and
(e) a handpiece positioned at and cooperating with said proximal end of said elongated member, said handpiece including first control means operatively connected through said elongated member with said moving means for causing said anvil member and said head assembly to move between said first and second positions; second control means operatively connected through said elongated member with said head assembly for causing said surgical staples to be advanced from said staple slots toward said anvil pockets; and viewing means operatively connected through said elongated member with said imaging means for viewing said interior body region image.

55. The endoscopic surgical stapler of claim 54, wherein said imaging means is mounted to said head assembly.

56. The endoscopic surgical stapler of claim 55, wherein said anvil member includes an aperture which is adapted to align with said imaging means, said aperture permitting said imaging means to obtain said image therethrough.

57. The endoscopic surgical stapler of claim 56, wherein said tissue engaging surface and tissue contacting surface are substantially circular, and wherein said imaging means is mounted at an interior position of said circular tissue contacting surface.

58. The endoscopic surgical stapler of claim 57, wherein said staple slots are positioned around the circumference of said circular tissue contacting surface, and said imaging means is mounted within a perimeter defined by said circumferentially positioned staple slots.

* * * * *